US011254954B2

(12) United States Patent
McKinlay et al.

(10) Patent No.: US 11,254,954 B2
(45) Date of Patent: Feb. 22, 2022

(54) CULTURE CONDITIONS THAT ALLOW ZYMOMONAS MOBILIS TO ASSIMILATE N2 GAS AS A NITROGEN SOURCE DURING BIO-ETHANOL PRODUCTION

(71) Applicant: Indiana University Research and Technology Corporation, Indianapolis, IN (US)

(72) Inventors: James McKinlay, Bloomington, IN (US); Amanda Posto, Stinesville, IN (US); Timothy Kremer, Bloomington, IN (US); Breah LaSarre, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/540,326

(22) PCT Filed: Dec. 21, 2015

(86) PCT No.: PCT/US2015/067100
§ 371 (c)(1),
(2) Date: Jun. 28, 2017

(87) PCT Pub. No.: WO2016/109286
PCT Pub. Date: Jul. 7, 2016

(65) Prior Publication Data
US 2018/0002728 A1 Jan. 4, 2018

Related U.S. Application Data

(60) Provisional application No. 62/098,634, filed on Dec. 31, 2014.

(51) Int. Cl.
| | | |
|---|---|---|
| C12P 7/06 | (2006.01) |
| C12N 1/20 | (2006.01) |
| C12N 1/38 | (2006.01) |
| C12P 7/10 | (2006.01) |
| C12P 7/04 | (2006.01) |
| C12P 7/16 | (2006.01) |

(52) U.S. Cl.
CPC ............... *C12P 7/065* (2013.01); *C12N 1/20* (2013.01); *C12N 1/38* (2013.01); *C12P 7/04* (2013.01); *C12P 7/10* (2013.01); *C12P 7/16* (2013.01); *Y02E 50/10* (2013.01)

(58) Field of Classification Search
CPC .... C12P 7/065; C12P 7/10; C12P 7/16; C12N 1/38; C12N 1/20
See application file for complete search history.

(56) References Cited

U.S. PATENT DOCUMENTS

| | | |
|---|---|---|
| 2007/0178569 A1 | 8/2007 | Leschine et al. |
| 2010/0244539 A1 | 9/2010 | Kardassilaris |
| 2010/0255553 A1 | 10/2010 | Srienc et al. |
| 2011/0252696 A1 | 10/2011 | Franklin et al. |
| 2012/0270303 A1 | 10/2012 | Hong et al. |
| 2013/0034884 A1 | 2/2013 | Burgard et al. |
| 2013/0130344 A1 | 5/2013 | Lee et al. |
| 2013/0177955 A1* | 7/2013 | Simpson ................... C12P 7/18 435/158 |
| 2014/0178955 A1 | 6/2014 | Rangaswamy et al. |
| 2014/0287467 A1 | 9/2014 | Medoff et al. |

FOREIGN PATENT DOCUMENTS

| | | |
|---|---|---|
| WO | 199850524 A1 | 11/1998 |
| WO | 2008028055 A2 | 3/2008 |
| WO | 2009059254 A2 | 5/2009 |

OTHER PUBLICATIONS

And Hugh G. Lawford, A new approach to improving the performance of Zymomonas in continuous ethanol fermentations. Applied Biochemistry and Biotechnology. (1988), 17: pp. 203-219.*
Davis et al. Evaluation of wheat stillage for ethanol production by recombinant Zymomonas mobilis. Biomass and Bioenergy 29 (2005) 49-59.*
Hugh G. Lawford A new approach to improving the performance of Zymomonas in continuous ethanol fermentation. Applied Biochemistry and Biotechnology 17, 203-219 (1988).*
Gordon, et al., Calvin Cycle Mutants of Photoheterotrophic Purple Nonsulpher Bacteria Fail to Grow Due to an Electron Imbalance Rather Than Toxic Metabolite Accumulation, Journal of Bacteriology, vol. 196, No. 6, 2014, pp. 1231-1237.
Lee, et al., The genome-scale metabolic network analysis of Zymomonas mobilis ZM4 explains physiological features and suggests ethanol and succinic acid production strategies, Microbial Cell Factories, 2010, vol. 9, No. 94, 12 pgs.
McKinlay, et al., Insights into Actinobacillus succinogenes Fermentative Metabolism in a Chemically Defined Growth Medium, Applied and Environmental Microbiology, Nov. 2005, pp. 6651-6656.
McKinlay, et al., Non-growing Rhodopseudomonas palustris Increases the Hydrogen Gas Yield from Acetate by Shifting from the Glyoxylate Shunt to the Tricarboxylic Acid Cycle, The Journal of Biological Chemistry, vol. 289, No. 4, pp. 1960-1970, 2014.
McKinlay, et al., Carbon dioxide fixation as a central redox cofactor recycling mechanism in bacteria, PNAS, 2010, vol. 107, No. 26, pp. 11669-11675.

(Continued)

*Primary Examiner* — Iqbal H Chowdhury
(74) *Attorney, Agent, or Firm* — Eric J. Kraus

(57) ABSTRACT

Chemically defined culture medium and culture conditions that allow bacteria to assimilate dinitrogen gas ($N_2$) as a nitrogen source during bio-ethanol production are disclosed herein. Methods of bioethanol production using the chemically defined culture medium and culture conditions are also disclosed.

19 Claims, 9 Drawing Sheets

(56) References Cited

OTHER PUBLICATIONS

McKinlay, et al., Determining Actinobacillus succinogenes metabolic pathways and fluxes by NMR and GC-MS analyses of C-labeled metabolic product isotopomers, Metabolic Engineering, vol. 9, 2007, pp. 177-192.
Millard, et al., IsoCor: correcting MS data in isotope labeling experiments, vol. 29, No. 9, 2012, pp. 1294-1296.
Schwender, et al., Mitochondrial Metabolism in Developing Embryos of Brassica napus, The Journal of Biological Chemistry, vol. 281, No. 45, pp. 34040-34047, 2006.
Sedlak, et al., Production of Ethanol from Cellulosic Biomass Hydrolysates Using Genetically Engineered *Saccharomyces* Yeast Capable of Cofermenting Glucose and Xylose, Applied Biochemistry and Biotechnology, vol. 113-116, 2004, pp. 403-416.
Weitzel, et al., 13CFLUX2-high-performance software suite for C-metabolic flux analysis, Bioinformatics, vol. 29, No. 1, 2013, pp. 143-145.

\* cited by examiner

CULTURE CONDITIONS THAT ALLOW ZYMOMONAS MOBILIS TO ASSIMILATE N2 GAS AS A NITROGEN SOURCE DURING BIO-ETHANOL PRODUCTION

CROSS-REFERENCE TO RELATED APPLICATIONS

This application claims priority to International Application Number PCT/US2015/067100, filed on 21 Dec. 2015, which claims priority to U.S. Provisional Patent Application No. 62/098,634, filed Dec. 31, 2014, the disclosure of both of which is incorporated by reference in its entirety.

STATEMENT REGARDING FEDERALLY SPONSORED RESEARCH & DEVELOPMENT

This invention was made with government support under DE-SC0008131 awarded by the Department of Energy. The Government has certain rights in the invention.

BACKGROUND OF THE DISCLOSURE

The field of the disclosure relates generally to growth conditions for bacterial bio-ethanol production. Particularly, bacteria are grown under anaerobic conditions in a medium that has little or no soluble nitrogen compounds (e g , ammonium), but supplemented with iron (Fe) and molybdenum (Mo), under a $N_2$ headspace.

More ethanol is produced than any other bio-fuel in the world, with production rates nearly 4-times that of biodiesel. Most ethanol is currently produced from starch from food crops using fermentative yeast such as *Saccharomyces cerevisiae*. Ethanol derived from food crops can be referred to as grain ethanol. Recently, there has been a surge in ethanol production from non-food crops, known as cellulosic feedstocks or lignocellulosic feedstocks. Ethanol derived from cellulosic feedstocks can be referred to as cellulosic ethanol. Cellulosic ethanol offers more favorable land use than grain ethanol because the non-food crops do not have to compete for land against crops grown for food. Furthermore, cellulosic ethanol production offers lower greenhouse gas emissions as compared to the production of grain ethanol. Unfortunately, the price of cellulosic ethanol remains high relative to that of gasoline. Efforts to lower the cost of cellulosic ethanol have primarily focused on the largest cost contributors, such as plant feedstocks and the cellulases needed to break them down into usable sugars.

Further, cellulosic feedstocks have low nitrogen contents, and thus, have to be enriched with nitrogen supplements to allow the ethanol-producing microbes to grow. These supplements further incur a large cost for cellulosic ethanol plants. For example, cellulosic feedstocks must be enriched with nitrogen supplements such as corn steep liquor (CSL), diammonium phosphate (DAP), ammonium hydroxide and/ or other ammonium salts. A facility that produces over 50 MM gallons of ethanol per year has been estimated to incur CSL and diammonium phosphate costs between $1.7-1.9 million per year. Other analyses estimated even higher CSL costs between $7.7-18.2 million per year. Furthermore, there are projections that the supply of CSL could not scale to support operations of billions of gallons of ethanol per year. Thus, a sustainable alternative nitrogen source is desired.

Nitrogen gas ($N_2$) is recognized as a sustainable source of nitrogen for agriculture as leguminous crops can be exploited for the symbiotic relationships they form with $N_2$-fixing bacteria. $N_2$-fixing bacteria are able to use $N_2$ gas as a nitrogen source via the enzyme, nitrogenase. $N_2$ gas could also serve as an economical and environmentally benign nitrogen source for industrial fermentations. For example, pure $N_2$ could be produced on-site for $0.06-0.21 per 100 cubic feet of gas. However, like all yeast, the industrial ethanol-producing yeast are incapable of using $N_2$ as a nitrogen source. Thus, there is a need for an ethanol-producing microbe that uses $N_2$ as a nitrogen source.

Based on the foregoing, there is a need in the art for alternative methods for producing ethanol, as well as higher chain alcohols, such as butanol. It would be further beneficial to reduce or eliminate the need for added nitrogen supplements to ethanol-producing fermentations and other industrial bioprocesses such to provide additional cost savings.

BRIEF DESCRIPTION OF THE DISCLOSURE

It has now been found that *Zymomonas mobilis* (*Z. mobilis*) can be grown in anaerobic medium lacking soluble nitrogen compounds (e g , ammonium) and supplemented with iron (Fe) and molybdenum (Mo) under a $N_2$ headspace. Further, these conditions allow for N2 fixation during anaerobic fermentation via nitrogenase. Particularly, the $N_2$-fixing capacity of *Z. mobilis* can eliminate the need for nitrogen supplements, such as CSL, DAP, and ammonium, thereby allowing for a more effective, cost-efficient bio-ethanol production process.

Accordingly, in one aspect, the present disclosure is directed to a chemically defined culture medium comprising iron and molybdenum. In one embodiment, the chemically defined culture medium comprises: $Na_2HPO_4$ (5.75 mM), $KH_2PO_4$ (7 mM), NaCl (8.6 mM), calcium pantothenate (105 nM), $MgSO_4$ (1 mM), $CaCl_2$ (0.1 mM) and trace elements 0.1% (v/v), wherein the trace elements comprise: nitrilotriacetic acid (20 g/L), $MgSO_4$ (28.9 g/L), $CaCl_2 \cdot 2H_2O$ (6.67 g/L), $(NH_4)_6Mo_7O_{24} \cdot 4H_2O$ (18.5 mg/L), $FeSO_4 \cdot 7H_2O$ (198 mg/L), and Metals 44 (0.1% v/v). Metals 44 is comprised of: ethylenediaminetetraacetic acid (2.5 µg/L), $ZnSO_4 \cdot 7H_2O$ (10.95 µg/L), $FeSO_4 \cdot 7H_2O$ (5 µg/L), $MnSO_4 \cdot H_2O$ (1.54 µg/L), $CuSO_4 \cdot 5H_2O$ (0.392 µg/L), $Co(NO_3)_2 \cdot 6H_2O$ (0.25 µg/L), and $Na_2B_4O_7 \cdot 10H_2O$ (0.177 µg/L). The above medium may be supplemented with either $NH_4Cl$ (10 mM) or $N_2$ gas as a nitrogen source in sealed vessels under anaerobic conditions.

In another aspect, the present disclosure is directed to a method of alcohol production. The method comprises: growing bio-fuel producing bacteria in a chemically defined culture medium in the presence of a nitrogen source, wherein the chemically defined culture medium comprises iron (Fe) and molybdenum (Mo) and wherein the nitrogen source comprises $N_2$ gas.

In another aspect, the present disclosure is directed to a method of alcohol production. The method comprising: growing bio-fuel producing bacteria in a hydrolysate of a cellulosic feedstock in the presence of a nitrogen source wherein the nitrogen source comprises $N_2$ gas, with iron (Fe) and molybdenum (Mo).

BRIEF DESCRIPTION OF THE DRAWINGS

(FIG. 3A) Growth (gray squares), glucose consumption (black triangles), and ethanol production (black circles) when provided $NH_4^+$ (closed symbols) or $N_2$ (open symbols) in an anaerobic chemically defined medium. Error bars are s.d. (n=4). (FIG. 3B) Relative abundances for the M-57 fragment of tert-butyl-dimethylsilyl-alanine (inset image; alanine atoms in bold) normalized to the most abundant ion. Alanine was obtained from acid hydrolysis of *Z. mobilis* protein. Gray, unlabeled standard; black, *Z. mobilis* grown with $^{15}N_2+NH_4^+$; white, *Z. mobilis* grown with $^{15}N_2$. The 10% residual abundance at m/z 260 (white) is due to unlabeled $N_2$ in the test tubes (9 +/-5% of the $N_2$) and unlabeled N from the inoculum (0.9 +/-0.1% of the cells). All 12 amino acids analyzed showed similar distributions (Table 2). Error bars are s.d. (n=3).

DETAILED DESCRIPTION OF THE DISCLOSURE

Figure 1:
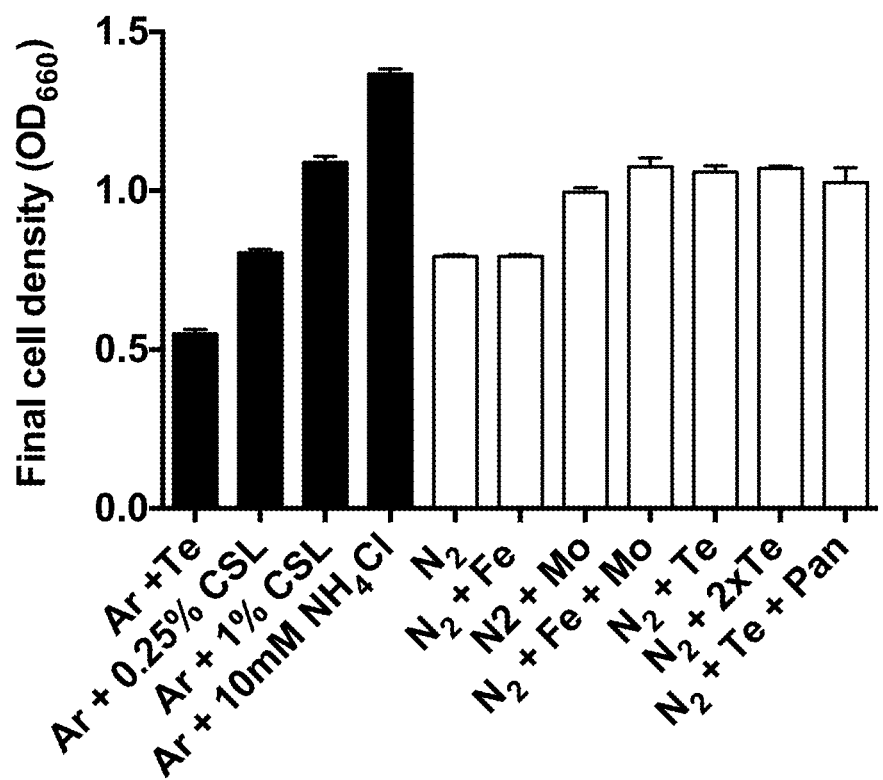
FIG. 1 depicts growth in miscanthus hydrolysate that simulates the available nitrogen in an industrial cellulosic hydrolysate when Ar (black) or $N_2$ (white) headspace was provided with various supplements as analyzed in the Examples. The final cell density represents the final optical density ($OD_{660}$) when all glucose was consumed minus the initial $OD_{660}$. Error bars are s.d. (n=4). Te, trace elements, as used in the chemically defined medium: Fe, 0.71 mg/L $FeSO_4·7H_2O$; Mo, 0.026 mg/L $(NH_4)_6Mo_7O_{24}·4H_2O$; Pan, 105 nM calcium pantothenate.

The present disclosure is generally related to culture medium and growth conditions that allow for $N_2$ fixation during anaerobic fermentation. Particularly, it has been found that, in one embodiment, a chemically defined culture medium can be prepared that allows bacteria to use nitrogenase to assimilate dinitrogen gas ($N_2$) as the sole nitrogen source during bio-ethanol production. It is believed that growing an ethanol-producing microbe with the capacity to fix $N_2$ can provide for a more effective, cost-efficient bio-ethanol production process since $N_2$ could be produced at an ethanol production facility for a fraction of the cost of typical industrial nitrogen supplements.

The present disclosure solves the problematic spending of millions of dollars on industrial nitrogen supplements by providing a culture medium and growth conditions that allow for $N_2$ fixation during anaerobic production of biofuels by bacteria, particularly, ethanol production by Zymomonas mobilis. *Z. mobilis* is a bacterium that produces ethanol from glucose at near-theoretical maximum yields. *Z. mobilis* produces slightly more ethanol per glucose than yeast and 3-5-times faster on a per cell basis. *Z. mobilis* also produces less residual biomass during ethanol production than yeast. Strains of *Z. mobilis* have been engineered that can also consume 5-carbon sugars such as xylose and arabinose. These engineered strains can therefore use sugars derived from both cellulose and hemicellulose. *Z. mobilis* has long been viewed as a potential competitor to yeast. Recent advances in tools to genetically manipulate *Z. mobilis* and improve its tolerance to toxic byproducts formed during the hydrolysis of cellulosic feedstocks have positioned *Z. mobilis* to be an emerging competitor for ethanol production versus yeast.

Accordingly, in one embodiment, a chemically defined culture medium can be prepared that allows bacteria to use nitrogenase to assimilate dinitrogen gas ($N_2$) as a nitrogen source during bio-ethanol production. In some embodiments, $N_2$ is the sole nitrogen source during bio-ethanol production. In other embodiments, $N_2$ may be used as the nitrogen source as a supplement to other nitrogen sources that are present in limiting amounts, such that N2 can be used when the other nitrogen sources are used up.

Generally, the chemically defined culture medium for use in the present disclosure may be a chemically defined minimal medium supplemented with iron (Fe) and molybdenum (Mo), which are the two metal cofactors required for nitrogenase activity. As used herein, "chemically defined culture medium" refers to a growth medium in which all of the chemical components, as well as their exact concentrations, are known.

Particularly, the chemically defined culture medium of one embodiment of the present disclosure includes: $Na_2HPO_4$ (5.75 mM), $KH_2PO_4$ (7 mM), NaCl (8.6 mM), and trace elements 0.1% (v/v). The trace elements solution contains: nitrilotriacetic acid (20 g/L), $MgSO_4$ (28.9 g/L), $CaCl_2·2H_2O$ (6.67 g/L), $(NH_4)_6Mo_7O_{24}·4H_2O$ (18.5 mg/L), $FeSO_4·7H_2O$ (198 mg/L), Metals 44 (0.1% v/v). Metals 44 is comprised of: ethylenediaminetetraacetic acid (2.5 g/L), $ZnSO_4·7H_2O$ (10.95 g/L), $FeSO_4·7H_2O$ (5 g/L), $MnSO_4·H_2O$ (1.54 g/L), $CuSO_4·5H_2O$ (0.392 g/L), $Co(NO_3)_2·6H_2O$ (0.25 g/L), $Na_2B_4O_7·10H_2O$ (0.177 g). After autoclaving, the following supplements were added (final concentrations): calcium pantothenate (105 nM), $MgSO_4$ (1 mM), and $CaCl_2$ (0.1 mM).

Alternatively, calcium pantothenate can be replaced by 0.01% v/v corn steep liquor.

The chemically defined culture medium can further be supplemented with either $NH_4Cl$ (10 mM) or $N_2$ headspace as a nitrogen source. When $NH_4Cl$ is not provided, an equimolar concentration of NaCl is provided to maintain similar osmotic conditions, if desired.

In some particularly suitable embodiments, the culture medium is supplemented with 100% $N_2$ headspace as a nitrogen source. It should be recognized by one skilled in the art, however, that lower concentrations (e.g., less than 100%, less than 95%, less than 90% or lower) of $N_2$ headspace may be used as long as $O_2$ gas is not present at concentrations that would prevent nitrogenase function. Particularly suitable $N_2$ gas concentration ranges from about 0.45 mM (per liter of culture liquid) to about 76 mM (per liter of culture liquid), including from about 13.4 mM (per liter of culture liquid) to about 76 mM (per liter of culture liquid).

In an alternative embodiment, a reactor sparged with $N_2$ to supply the nitrogen source.

Alternatively, the culture medium can be a hydrolysate of a cellulosic feedstock supplemented with iron and molybdenum under a $N_2$ headspace or sparged with $N_2$. Suitable cellulosic feedstock materials include any non-food, cellulose rich material such as switchgrass, miscanthus, corn stover, poplar, rice straw, sorghum, wheat straw, wood chips, sawdust, newspaper, other wood and paper products, other agricultural residues, and the like, and combinations thereof. Cellulose can be released from lignin and hemicellulose, and hemicellulose can be hydrolyzed to sugar monomers using pretreatment methods such as acid hydrolysis, alkaline hydrolysis, liquid hot water, steam explosion, ammonia fiber explosion and the like, and combinations thereof. A secondary hydrolysis would follow the pretreatment to release sugar monomers from the cellulose. Secondary hydrolysis would make use of enzymes, including cellulases. The molybdenum and iron minerals could be $(NH_4)_6Mo_7O_{24} \cdot 4H_2O$ (0.0185 mg/L) and $FeSO_4 \cdot 7H_2O$ (0.198 mg/L) or other molybdenum and iron-containing minerals.

Figure 2A:
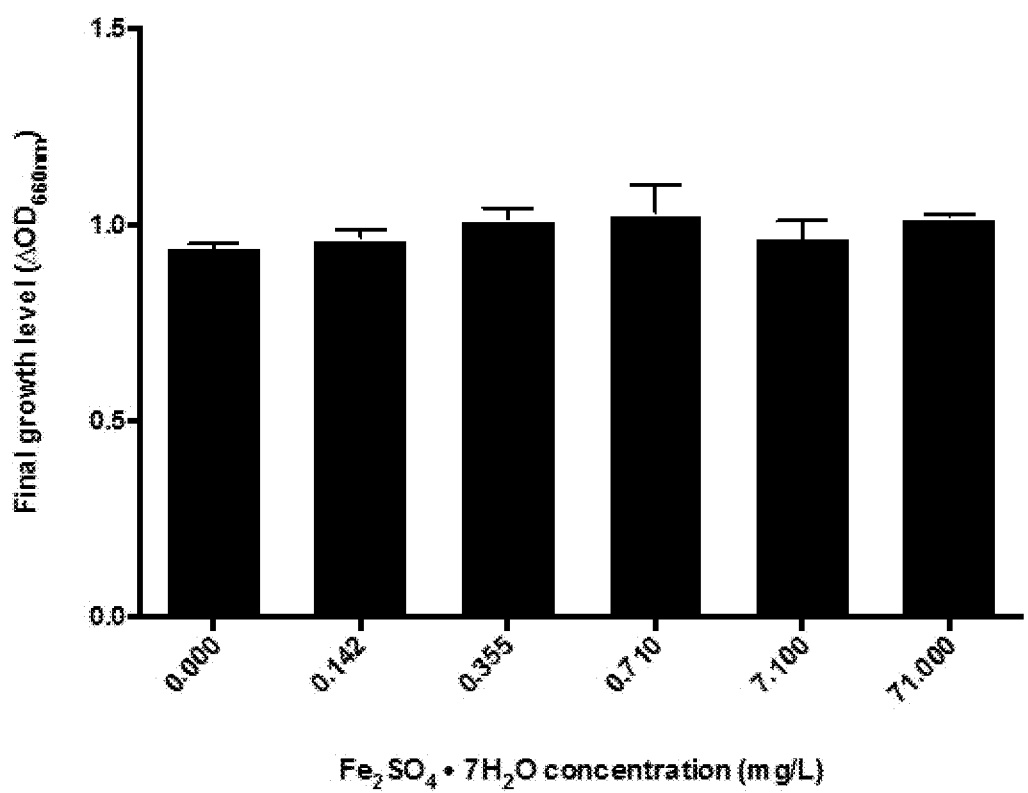
FIGS. 2A & 2B depict iron and molybdenum concentrations that limit growth of $N_2$-fixing *Zymomonas mobilis* (ZM4) in miscanthus hydrolysate medium.
Figure 2B:
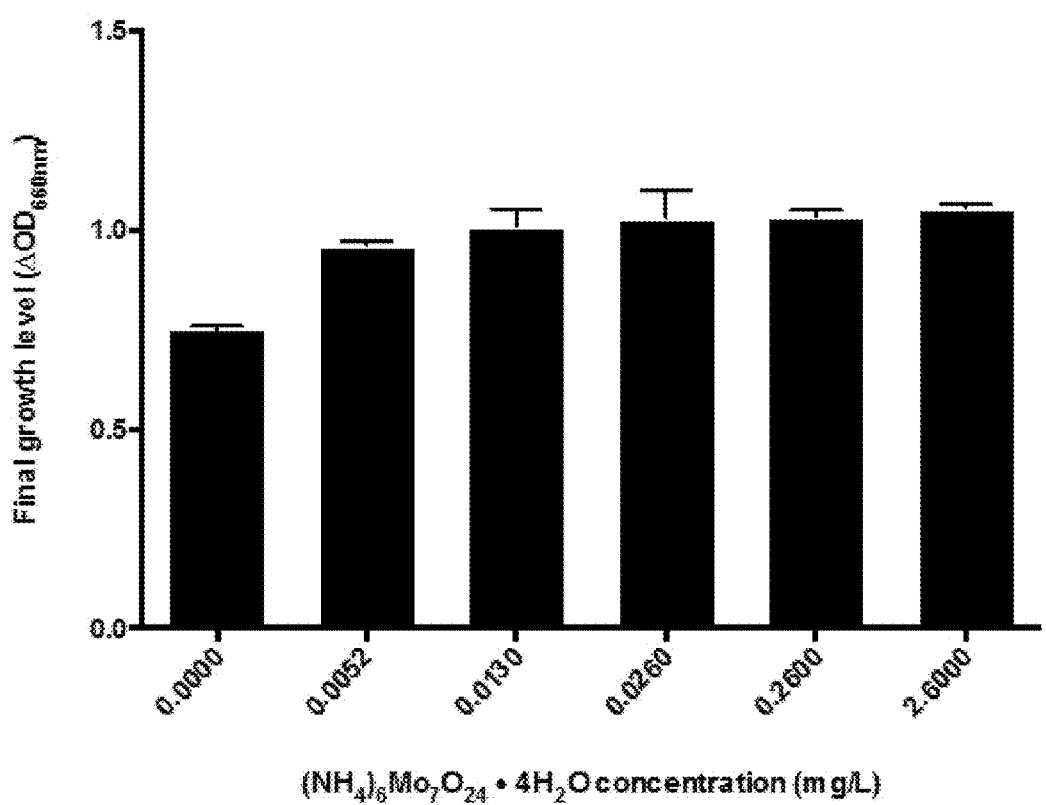

In one embodiment of the disclosure, a hydrolysate medium derived from miscanthus grass was found to contain sufficient pantothenate to support full growth of *Z. mobilis* but insufficient iron (Fe) and molybdenum (Mo) (see FIG. 1). The Fe and Mo concentrations that limit growth of $N_2$-fixing *Z. mobilis* (ZM4) in miscanthus hydrolysate medium were identified (see FIG. 2). Particularly, miscanthus hydrolysate was prepared as described in the Examples below with $N_2$ as the major nitrogen source and with three separate glucose supplements to simulate sugar that would be released by cellulases. For iron-limitation experiments (FIG. 2A) the $(NH_4)_6Mo_7O_{24} \cdot 4H_2O$ concentration was constant at 0.026 mg/L. For molybdenum-limitation experiments (FIG. 2B) the $FeSO_4 \cdot 7H_2O$ concentration was constant at 0.71 mg/L. The minimum concentration of $(NH_4)_6Mo_7O_{24} \cdot 4H_2O$ and $FeSO_4 \cdot 7H_2O$ to support full growth of *Z. mobilis* in miscanthus hydrolysate were identified as 0.026 mg/L and 0.355 mg/L, respectively (see FIG. 2).

Generally, the microorganisms for use with the culture medium can be any bio-fuel producing bacteria or archaea as known in the art. As referred to herein, "a bio-fuel producing microorganism", "a bio-fuel producing bacterium", and "bio-fuel producing archaeon" include microorganisms including bacteria and archaea that are capable of producing ethanol as well as higher chain alcohols, such as propanol, butanol and biodiesels, through the fermentation of sugars or starches, or polysaccharides such as cellulose, hemicellulose, or syngas. As referred to herein, "bio-fuel producing bacteria" and "bio-fuel producing archaea" include bacteria and archaea that can use $N_2$ as a nitrogen source. In one particularly suitable embodiment, the bacterium is *Zymomonas mobilis*, particularly, *Z. mobilis* ZM4. In another embodiment, the bacterium is another strain of *Z. mobilis*. In yet another embodiment, the bacterium is an engineered strain of *Z. mobilis* that is capable of fermenting both hexose and pentose sugars and shows higher resistance to toxic compounds such as acetic acid and furfurals. In another embodiment, the bacterium is a bio-fuel-producing bacterium that is not of the genus *Zymomonas*. Such bacteria could include ethanol and butanol-producing bacteria, such as *Acetobacterium woodii*, *Ruminococcus albus*, *Fibrobacter succinogenes*, and various *Clostridia* such as *Clostridium phytofermentans*, *C. kluyverii*, *C. pasteurianum*, *C. beijerinckii*, *C. autoethanogenum*, *C. ljungdahlii*, *C. carboxidivorans*, and *C. acetobutlylicum*.

In another aspect, the present disclosure is directed to a method of alcohol production. The method includes: growing a bio-fuel producing microorganism in a chemically defined culture medium in the presence of a nitrogen source, wherein the chemically defined culture medium comprises iron and molybdenum and wherein the nitrogen source is $N_2$ gas.

Suitable bacteria bio-fuel producing microorganisms include bio-fuel producing bacteria and bio-fuel producing archaea as described herein.

A particularly suitable $N_2$ gas of the method is provided as a $N_2$ gas headspace. Particularly suitable $N_2$ gas concentration ranges from about 0.45 mM (per liter of culture liquid) to about 76 mM (per liter of culture liquid).

The chemically defined culture medium further includes: $Na_2HPO_4$, $KH_2PO_4$, and NaCl in a molar ratio of about 1:1.2:1.5. The chemically defined culture medium suitably includes $Na_2HPO_4$, $KH_2PO_4$, NaCl, and trace elements, wherein the trace elements comprise: nitrilotriacetic acid, $MgSO_4$, $CaCl_2 \cdot 2H_2O$, $(NH_4)_6Mo_7O_{24} \cdot 4H_2O$, $FeSO_4 \cdot 7H_2O$, ethylenediaminetetraacetic acid, $ZnSO_4 \cdot 7H_2O$, $FeSO_4 \cdot 7H_2O$, $MnSO_4 \cdot H_2O$, $CuSO_4 \cdot 5H_2O$, $Co(NO_3)_2 \cdot 6H_2O$, and $Na_2B_4O_7 \cdot 10H_2O$, as described herein.

The method can further include autoclaving the chemically defined culture medium. The method can further include providing calcium pantothenate, $MgSO_4$, and $CaCl_2$ to the autoclaved chemically defined culture medium.

The alcohol produced can be propanol, ethanol and butanol.

The method can further include growing the bio-fuel producing microorganism at a temperature ranging from about 20° C. to about 40° C.

The method can further include growing the bio-fuel producing microorganism at a pH ranging from about 4 to about 9.2.

In another aspect, the present disclosure is directed to a method of alcohol production, the method comprising: growing a bio-fuel producing microorganism in a hydrolysate of a cellulosic feedstock in the presence of a nitrogen source, wherein the nitrogen source is $N_2$ gas.

Suitable bacteria bio-fuel producing microorganisms include bio-fuel producing bacteria and bio-fuel producing archaea as described herein.

A particularly suitable $N_2$ gas of the method is provided as a $N_2$ gas headspace. Particularly suitable $N_2$ gas concentration ranges from about 0.45 mM to about 76 mM.

A particularly suitable hydrolysate of a cellulosic feedstock can be, for example, a hydrolysate of *Miscanthus x giganteus*.

The hydrolysate can further include iron and molybdenum.

The alcohol produced can be propanol, ethanol and butanol.

It has unexpectedly been found that using the culture medium and conditions of the present disclosure allow for fixation of $N_2$ by bio-fuel producing bacteria during anaerobic fermentation, and this process results in decreased biomass, while high alcohol, and particularly, ethanol, yield is maintained. It has further been found that the specific rate of alcohol production is faster during $N_2$ fixation than when conventional nitrogen sources, such as ammonium, are present.

Various functions and advantages of these and other embodiments of the present disclosure will be more fully understood from the examples described below. The following examples are intended to illustrate the benefits of the present disclosure, but do not exemplify the full scope of the disclosure.

EXAMPLES

Example 1

In this Example, the ability of *Zymomonas mobilis* (*Z. mobilis*) to grow in chemically-defined minimal medium and fix $N_2$ was analyzed.

$^{15}N_2$ was purchased from Cambridge Isotope Laboratories (Tewskbury, Mass.). All other chemicals were purchased from Sigma-Aldrich (St. Louis, Mo.) or Fisher Scientific (Waltham, Mass.).

*Zymomonas mobilis* (ZM4) was obtained from the ARS Culture Collection. Cultures were grown in 10-ml volumes in 27-ml anaerobic test tubes or in 60-ml volumes in 160-ml serum vials at 30° C. Media were made anaerobic by bubbling with either $N_2$ or Ar and sealed with rubber stoppers and aluminum crimps as described in Gordon & McKinlay (Bacteriol. 196:1231-1237 (2014)). Test tubes were laid flat and serum vials were left upright. All cultures were shaken at 225 rpm.

The chemically defined medium (ZYMM) contained: $Na_2HPO_4$ (5.75 mM), $KH_2PO_4$ (7 mM), NaCl (8.6 mM), and trace elements 0.1% (v/v). The trace elements solution contained: nitrilotriacetic acid (20 g/L), $MgSO_4$ (28.9 g/L), $CaCl_2 \cdot 2H_2O$ (6.67 g/L), $(NH_4)_6Mo_7O_{24} \cdot 4H_2O$ (18.5 mg/L), $FeSO_4 \cdot 7H_2O$ (198 mg/L), Metals 44 (0.1% v/v). Metals 44 is comprised of: ethylenediaminetetraacetic acid (2.5 g/L), $ZnSO_4 \cdot 7H_2O$ (10.95 g/L), $FeSO_4 \cdot 7H_2O$ (5 g/L), $MnSO_4 \cdot H_2O$ (1.54 g/L), $CuSO_4 \cdot 5H_2O$ (0.392 g/L), Co$(NO_3)_2 \cdot 6H_2O$ (0.25 g/L), $Na_2B_4O_7 \cdot 10H_2O$ (0.177 g/L). After autoclaving, the following supplements were added (final concentrations): calcium pantothenate (105 nM), $MgSO_4$ (1 mM), and $CaCl_2$ (0.1 mM). ZYMM was supplemented with either $NH_4Cl$ (10 mM) or a 100% $N_2$ headspace as a nitrogen source. When $NH_4Cl$ was not provided, an equimolar concentration of NaCl was provided to maintain similar osmotic conditions.

To introduce $^{15}N_2$ gas, a stir bar was inserted into the neck of the breakseal flask that the $^{15}N_2$ was shipped in and then a sampling port was attached to the neck. The sampling port consisted of a 5-ml tuberculin syringe with the plunger replaced by a rubber stopper (Geo-Microbial Technologies, Ochelata, Okla.) that was connected to the breakseal flask neck by rubber tubing. The stir bar was then used to break the seal. The headspace in anaerobic test tubes containing anaerobic media was evacuated with a vacuum pump. For each addition of gas to an anaerobic test tube, the breakseal flask was over-pressurized with 15-ml of Ar using a syringe to displace the $^{15}N_2$ into the sampling port. 15 ml of the resulting $^{15}N_2$/Ar mixture was then transferred to the evacuated test tube via syringe.

*Z. mobilis* was inoculated into anaerobic chemically defined medium containing the metal cofactors for nitrogenase (i.e., Mo and Fe). Cell density was assayed by optical density at 660 nm using a Genesys 20 visible spectrophotometer (Thermo-Fisher). Dry cell weights were determined as described in McKinlay et al. (Metab. Eng. 9:177-192 (2007)). Optical densities were converted into dry cell weights using experimentally determined conversion factors of 516 mg DCW/L/$OD_{660}$ for cultures grown with $NH_4^+$ and 423 mg DCW/L/$OD_{660}$ for cultures grown with $N_2$. Electron recoveries were calculated based on available electrons as described in McKinlay & Harwood (Proc. Natl. Acad. Sci. U S A 107:11669-11675 (2010)), assuming an elemental composition of $CH_{1.125}O_{0.531}N_{0.214}$ (MW: 24.625 g/mole) for *Z. mobilis* biomass. Isotopic enrichments ($^{15}N$) in amino acids were determined by gas chromatography-mass spectrometry (Agilent) as described in McKinlay (Metab. Eng. 9:177-192 (2007)).

Figures 3A, 3B:
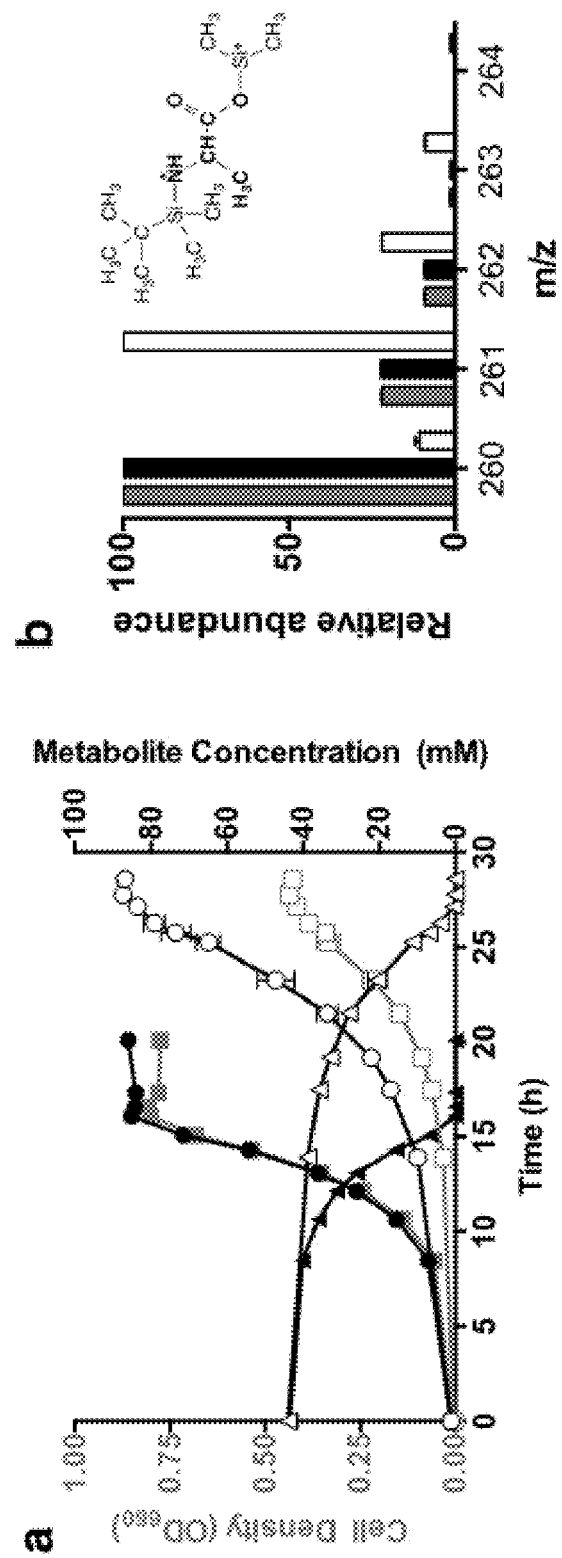
FIGS. 3A & 3B depict utilization of $N_2$ gas by *Z. mobilis* (ZM4).

As shown in FIG. 3A, *Z. mobilis* grew with either $NH_4^+$ or $N_2$. The growth rate with $N_2$ was about half that observed during growth with $NH_4^+$ (Table 1). No growth was observed when $NH_4^+$ and $N_2$ were omitted (Ar headspace) (data not shown). When *Z mobilis* was cultured with $^{15}N_2$, GC-MS analysis of amino acids from whole cell protein showed a mass shift of +1 (FIG. 3B; Table 2). This assimilation of $^{15}N_2$ confirmed that *Z. mobilis* can fix $N_2$ and that growth was not due to contaminating nitrogen sources. No mass shift was observed when $NH_4^+$ and $^{15}N_2$ were provided together (FIG. 3B).

TABLE 1

Comparison of growth and metabolic parameters during growth with $NH_4^+$ vs. $N_2$.

| Nitrogen source | Growth rate ($h^{-1}$) | Growth yield (g DCW × mole glucose$^{-1}$) | Ethanol yield (mole × mole glucose$^{-1}$) | Ethanol:Biomass (mmole × g DCW$^{-1}$) | Sp. Ethanol productivity (mmole × g DCW$^{-1}$ × h$^{-1}$) | Sp. Glucose consumption rate (mmol × g CDW$^{-1}$ × h$^{-1}$) | Carbon Recovery (%) | Electron Recovery (%) |
|---|---|---|---|---|---|---|---|---|
| $NH_4^+$ | 0.35 ± 0.02 | 9.5 ± 0.2 | 1.88 ± 0.08 | 198 ± 4 | 68.5 ± 3.8 | 36.43 ± 0.16 | 100 ± 4 | 101 ± 4 |
| $N_2$ | 0.22 ± 0.01 | 4.3 ± 0.1 | 1.95 ± 0.03 | 450 ± 17 | 99.5 ± 2.05 | 50.99 ± 0.11 | 100 ± 2 | 102 ± 2 |

Errors are s.d. (n = 4).
DCW, dry cell weight.

TABLE 2

Normalized mass isotopomer distributions in proteinaceous amino acids from $^{15}N_2$ labeling experiments. The amino group is always on carbon 2. Values are normalized to the most abundant ion. The distributions shown have not been corrected for natural isotopic abundances.

| Amino acid | Fragment (m/z) | C | m+ | Amino acid standard Ave | sd | $^{15}N_2 + NH_4^+$ Ave | sd | $^{15}N_2$ Ave | sd |
|---|---|---|---|---|---|---|---|---|---|
| Ala | 232 | 2, 3 | 0 | 100 | 0 | 100 | 0 | 11 | 1 |
|  |  |  | 1 | 22 | 0 | 22 | 0 | 100 | 0 |
|  |  |  | 2 | 9 | 0 | 9 | 0 | 22 | 0 |
|  |  |  | 3 | 1 | 0 | 1 | 0 | 9 | 0 |
|  | 260 | 1-3 | 0 | 100 | 0 | 100 | 0 | 11 | 1 |
|  |  |  | 1 | 23 | 0 | 23 | 0 | 100 | 0 |
|  |  |  | 2 | 9 | 0 | 10 | 0 | 23 | 0 |
|  |  |  | 3 | 1 | 0 | 1 | 0 | 9 | 0 |
| Gly | 218 | 2 | 0 | 100 | 0 | 100 | 0 | 11 | 1 |
|  |  |  | 1 | 21 | 0 | 21 | 0 | 100 | 0 |
|  |  |  | 2 | 9 | 0 | 9 | 0 | 21 | 0 |
|  |  |  | 3 | 1 | 0 | 1 | 0 | 9 | 0 |
|  | 246 | 1, 2 | 0 | 100 | 0 | 100 | 0 | 12 | 1 |
|  |  |  | 1 | 22 | 0 | 22 | 0 | 100 | 0 |
|  |  |  | 2 | 9 | 0 | 9 | 0 | 22 | 0 |
|  |  |  | 3 | 1 | 0 | 1 | 0 | 9 | 0 |
| Val | 186 | 2-5 | 0 | 100 | 0 | 100 | 0 | 10 | 2 |
|  |  |  | 1 | 17 | 0 | 17 | 0 | 100 | 0 |
|  |  |  | 2 | 5 | 0 | 5 | 0 | 17 | 0 |
|  |  |  | 3 | 1 | 0 | 2 | 0 | 6 | 0 |
|  |  |  | 4 | 0 | 0 | 0 | 0 | 1 | 0 |
|  | 260 | 2-5 | 0 | 100 | 0 | 100 | 0 | 9 | 1 |
|  |  |  | 1 | 25 | 0 | 25 | 0 | 100 | 0 |
|  |  |  | 2 | 10 | 0 | 10 | 0 | 24 | 0 |
|  |  |  | 3 | 1 | 1 | 2 | 0 | 10 | 0 |
|  |  |  | 4 | 0 | 0 | 0 | 0 | 2 | 0 |
|  |  |  | 5 | 0 | 0 | 0 | 0 | 0 | 0 |
|  |  |  | 6 | 0 | 0 | 0 | 0 | 0 | 0 |
|  | 288 | 1-5 | 0 | 100 | 0 | 100 | 0 | 10 | 1 |
|  |  |  | 1 | 25 | 0 | 25 | 0 | 100 | 0 |
|  |  |  | 2 | 9 | 2 | 10 | 0 | 25 | 0 |
|  |  |  | 3 | 1 | 0 | 2 | 0 | 10 | 0 |
|  |  |  | 4 | 0 | 0 | 0 | 0 | 2 | 0 |
| Leu | 200 | 2-6 | 0 | 100 | 0 | 100 | 0 | 9 | 1 |
|  |  |  | 1 | 18 | 0 | 18 | 0 | 100 | 0 |
|  |  |  | 2 | 6 | 0 | 6 | 0 | 18 | 0 |
|  |  |  | 3 | 1 | 0 | 1 | 0 | 6 | 0 |
|  |  |  | 4 | 0 | 0 | 0 | 0 | 1 | 0 |
|  | 274 | 2-6 | 0 | 100 | 0 | 100 | 0 | 10 | 1 |
|  |  |  | 1 | 25 | 0 | 25 | 0 | 100 | 0 |
|  |  |  | 2 | 10 | 0 | 10 | 0 | 25 | 0 |
|  |  |  | 3 | 2 | 0 | 2 | 0 | 10 | 0 |
|  |  |  | 4 | 0 | 0 | 0 | 0 | 2 | 0 |
| Ile | 200 | 2-6 | 0 | 100 | 0 | 100 | 0 | 9 | 1 |
|  |  |  | 1 | 18 | 0 | 18 | 0 | 100 | 0 |
|  |  |  | 2 | 5 | 0 | 5 | 0 | 18 | 0 |
|  |  |  | 3 | 1 | 0 | 1 | 0 | 5 | 0 |
|  |  |  | 4 | 0 | 0 | 0 | 0 | 1 | 0 |
|  | 274 | 2-6 | 0 | 100 | 0 | 100 | 0 | 9 | 1 |
|  |  |  | 1 | 38 | 0 | 26 | 0 | 100 | 0 |
|  |  |  | 2 | 6 | 0 | 10 | 0 | 25 | 0 |
|  |  |  | 3 | 1 | 0 | 2 | 0 | 10 | 0 |
|  |  |  | 4 | 0 | 0 | 0 | 0 | 2 | 0 |
| Met | 218 | 2-5 | 0 | 100 | 0 | 100 | 0 | 8 | 2 |
|  |  |  | 1 | 17 | 0 | 17 | 0 | 100 | 0 |
|  |  |  | 2 | 9 | 0 | 9 | 0 | 17 | 0 |
|  |  |  | 3 | 1 | 0 | 1 | 0 | 9 | 0 |
|  |  |  | 4 | 0 | 0 | 0 | 0 | 1 | 0 |
|  | 292 | 2-5 | 0 | 100 | 0 | 100 | 0 | 10 | 1 |
|  |  |  | 1 | 25 | 0 | 25 | 0 | 100 | 0 |
|  |  |  | 2 | 14 | 0 | 14 | 0 | 25 | 0 |
|  |  |  | 3 | 3 | 0 | 3 | 0 | 14 | 0 |
|  |  |  | 4 | 1 | 0 | 3 | 1 | 2 | 0 |
| Ser | 288 | 2, 3 | 0 | 100 | 0 | 100 | 0 | 10 | 1 |
|  |  |  | 1 | 26 | 0 | 26 | 0 | 100 | 0 |
|  |  |  | 2 | 10 | 0 | 10 | 0 | 26 | 0 |
|  |  |  | 3 | 2 | 0 | 2 | 0 | 10 | 0 |
|  |  |  | 4 | 0 | 0 | 0 | 0 | 2 | 0 |
|  | 302 | 1, 2 | 0 | 100 | 0 | 100 | 0 | 11 | 1 |
|  |  |  | 1 | 26 | 0 | 26 | 0 | 100 | 0 |
|  |  |  | 2 | 10 | 0 | 11 | 0 | 26 | 0 |
|  |  |  | 3 | 2 | 0 | 2 | 0 | 10 | 0 |
|  |  |  | 4 | 0 | 0 | 0 | 0 | 2 | 0 |
|  | 362 | 2, 3 | 0 | 100 | 0 | 100 | 0 | 9 | 1 |
|  |  |  | 1 | 33 | 0 | 31 | 2 | 100 | 0 |
|  |  |  | 2 | 16 | 0 | 15 | 0 | 34 | 0 |
|  |  |  | 3 | 3 | 0 | 3 | 0 | 13 | 1 |
|  |  |  | 4 | 1 | 0 | 1 | 0 | 3 | 0 |
|  | 390 | 1-3 | 0 | 100 | 0 | 100 | 0 | 10 | 1 |
|  |  |  | 1 | 35 | 0 | 35 | 0 | 100 | 0 |
|  |  |  | 2 | 16 | 0 | 16 | 0 | 35 | 0 |
|  |  |  | 3 | 4 | 0 | 4 | 0 | 16 | 0 |
|  |  |  | 4 | 1 | 0 | 1 | 0 | 4 | 0 |
|  |  |  | 5 | 0 | 0 | 0 | 0 | 1 | 0 |
| Thr | 376 | 2-4 | 0 | 100 | 0 | 100 | 0 | 9 | 1 |
|  |  |  | 1 | 34 | 0 | 35 | 0 | 100 | 0 |
|  |  |  | 2 | 16 | 0 | 16 | 0 | 34 | 0 |
|  |  |  | 3 | 4 | 0 | 4 | 0 | 16 | 0 |
|  |  |  | 4 | 1 | 0 | 1 | 0 | 3 | 0 |
|  | 404 | 1-4 | 0 | 100 | 0 | 100 | 0 | 9 | 1 |
|  |  |  | 1 | 36 | 0 | 36 | 0 | 100 | 0 |
|  |  |  | 2 | 16 | 0 | 17 | 0 | 36 | 0 |
|  |  |  | 3 | 4 | 0 | 4 | 0 | 16 | 0 |
|  |  |  | 4 | 1 | 0 | 1 | 0 | 4 | 0 |
|  |  |  | 5 | 0 | 0 | 0 | 0 | 1 | 0 |
| Phe | 234 | 2-9 | 0 | 100 | 0 | 100 | 0 | 10 | 1 |
|  |  |  | 1 | 21 | 0 | 21 | 0 | 100 | 0 |
|  |  |  | 2 | 6 | 0 | 6 | 0 | 21 | 0 |
|  |  |  | 3 | 1 | 0 | 1 | 0 | 6 | 0 |
|  |  |  | 4 | 0 | 0 | 0 | 0 | 1 | 0 |
|  | 302 | 1, 2 | 0 | 100 | 0 | 100 | 0 | 9 | 1 |
|  |  |  | 1 | 26 | 0 | 26 | 0 | 100 | 0 |
|  |  |  | 2 | 10 | 0 | 10 | 0 | 26 | 0 |
|  |  |  |  | 2 | 0 | 2 | 0 | 10 | 0 |
|  |  |  |  | 0 | 0 | 0 | 0 | 2 | 0 |
|  | 336 | 1-9 | 0 | 100 | 0 | 100 | 0 | 10 | 1 |
|  |  |  | 1 | 30 | 0 | 30 | 0 | 100 | 0 |
|  |  |  | 2 | 11 | 0 | 11 | 0 | 29 | 0 |
|  |  |  | 3 | 2 | 0 | 2 | 0 | 11 | 0 |
|  |  |  | 4 | 0 | 0 | 0 | 0 | 2 | 0 |
| Asp | 302 | 1, 2 | 0 | 100 | 0 | 100 | 0 | 9 | 1 |
|  |  |  | 1 | 26 | 0 | 27 | 0 | 100 | 0 |
|  |  |  | 2 | 11 | 0 | 11 | 0 | 27 | 0 |
|  |  |  | 3 | 2 | 0 | 2 | 0 | 10 | 0 |
|  |  |  | 4 | 0 | 0 | 0 | 0 | 2 | 0 |
|  | 316 | 2-4 | 0 | 100 | 0 | 100 | 0 | 10 | 1 |
|  |  |  | 1 | 27 | 0 | 28 | 0 | 100 | 0 |
|  |  |  | 2 | 11 | 0 | 11 | 0 | 27 | 0 |
|  |  |  | 3 | 3 | 0 | 3 | 0 | 11 | 0 |
|  |  |  | 4 | 1 | 0 | 1 | 0 | 2 | 0 |
|  |  |  | 5 | 0 | 0 | 0 | 0 | 1 | 0 |
|  | 390 | 2-4 | 0 | 100 | 0 | 100 | 0 | 9 | 1 |
|  |  |  | 1 | 34 | 0 | 35 | 0 | 100 | 0 |
|  |  |  | 2 | 16 | 0 | 16 | 0 | 35 | 0 |
|  |  |  | 3 | 4 | 0 | 4 | 0 | 16 | 0 |
|  |  |  | 4 | 1 | 0 | 1 | 0 | 4 | 0 |
|  |  |  | 5 | 0 | 0 | 0 | 0 | 1 | 0 |
|  | 418 | 1-4 | 0 | 100 | 0 | 100 | 0 | 9 | 1 |
|  |  |  | 1 | 36 | 0 | 36 | 0 | 100 | 0 |
|  |  |  | 2 | 17 | 0 | 17 | 0 | 36 | 0 |
|  |  |  | 3 | 4 | 0 | 4 | 0 | 17 | 0 |
|  |  |  | 4 | 1 | 0 | 1 | 0 | 4 | 0 |
|  |  |  | 5 | 0 | 0 | 0 | 0 | 1 | 0 |

TABLE 2-continued

Normalized mass isotopomer distributions in proteinaceous amino acids from $^{15}N_2$ labeling experiments. The amino group is always on carbon 2. Values are normalized to the most abundant ion. The distributions shown have not been corrected for natural isotopic abundances.

| Amino acid | Fragment (m/z) | Amino acid C | m+ | standard Ave | sd | $^{15}N_2$ + $NH_4^+$ Ave | sd | $^{15}N_2$ Ave | sd |
|---|---|---|---|---|---|---|---|---|---|
| Glu | 330 | 2-5 | 0 | 100 | 0 | 100 | 0 | 9 | 1 |
|  |  |  | 1 | 28 | 0 | 29 | 0 | 100 | 0 |
|  |  |  | 2 | 11 | 0 | 11 | 0 | 29 | 0 |
|  |  |  | 3 | 2 | 0 | 2 | 0 | 11 | 0 |
|  |  |  | 4 | 0 | 0 | 0 | 0 | 2 | 0 |
|  | 404 | 2-5 | 0 | 100 | 0 | 100 | 0 | 9 | 1 |
|  |  |  | 1 | 36 | 0 | 36 | 0 | 100 | 0 |
|  |  |  | 2 | 17 | 0 | 17 | 0 | 36 | 0 |
|  |  |  | 3 | 4 | 0 | 4 | 0 | 16 | 0 |
|  |  |  | 4 | 1 | 0 | 1 | 0 | 4 | 0 |
|  |  |  | 5 | 0 | 0 | 0 | 0 | 1 | 0 |
|  | 432 | 1-5 | 0 | 100 | 0 | 100 | 0 | 9 | 1 |
|  |  |  | 1 | 37 | 0 | 37 | 0 | 100 | 0 |
|  |  |  | 2 | 17 | 0 | 17 | 0 | 37 | 0 |
|  |  |  | 3 | 4 | 0 | 4 | 0 | 17 | 0 |
|  |  |  | 4 | 1 | 0 | 1 | 0 | 4 | 0 |
|  |  |  | 5 | 0 | 0 | 0 | 0 | 1 | 0 |
| Tyr | 302 | 1, 2 | 0 | 100 | 0 | 100 | 0 | 10 | 1 |
|  |  |  | 1 | 27 | 1 | 27 | 0 | 100 | 0 |
|  |  |  | 2 | 11 | 0 | 10 | 0 | 27 | 0 |
|  |  |  | 3 | 2 | 0 | 2 | 0 | 10 | 0 |
|  |  |  | 4 | 1 | 0 | 1 | 0 | 2 | 0 |

Example 2

In this Example, analysis of ethanol yield, rate, and intermediary metabolic fluxes from *Z. mobilis* (ZM4) fermentation during $N_2$-fixation in the chemically defined medium was conducted and compared to fermentation with ammonium.

Converting ½ $N_2$ into $NH_4^+$ requires 4 electrons and 8 ATP, which could impact various metabolic parameters. Accordingly, substrates and products were quantified using a Shimadzu high performance liquid chromatograph (HPLC analysis) as described in McKinlay et al. (Appl. Environ. Microbiol. 71:6651-6656 (2005)).

HPLC analysis of ZM4 supernatants showed that the ethanol yield was the same regardless of whether $NH_4^+$ or $N_2$ was provided (Table 1 above). Thus, electrons were not diverted away from ethanol production to support nitrogenase activity. Instead, electrons were diverted away from biosynthesis, as the growth yield with $N_2$ was 46% of that with $NH_4^+$(Table 1). The ratio of ethanol to biomass during growth with $N_2$ was over twice that observed with $NH_4^+$ (Table 1). Producing the same amount of ethanol with less residual biomass is a positive aspect for industrial ethanol production.

Remarkably, the specific ethanol production rate and the specific glucose consumption rate (Table 1) were both 1.45-fold higher during growth with $N_2$ versus $NH_4^+$. This higher metabolic rate may efficiently supply reducing power to both $N_2$ fixation and biosynthetic reactions. Growth with $N_2$ offers the industrial benefit of a higher specific ethanol production rate.

To determine if $N_2$ fixation affected intermediary metabolic fluxes, $^{13}$C-metabolic flux analysis was performed using two different isotopic mixtures. Cultures were grown in the defined medium with either 100% [1-$^{13}$C] glucose in one experiment and a mixture of 80% unlabeled and 20% uniformly labeled glucose. Isotopic enrichments ($^{13}$C) in amino acids were determined by gas chromatography-mass spectrometry (Agilent) as described in McKinlay (Metab. Eng. 9:177-192 (2007)). Intermediary metabolic fluxes were estimated from the glucose uptake rate, fermentation product ratios, the biomass composition for *Z. mobilis* ZM4 (Lee et al. Microb. Cell Fact. 9:94 (2010)), and mass isotopomer distributions from the parallel labeling experiments with the software, 13CFLUX2 (Weitzel et al. Bioinformatics 29:143-5 (2013)) using the NAGNLP optimizer found in the NAGC library as described in McKinlay et al. (J. Biol. Chem. 289:1960-70 (2014)). Mass isotopomer distributions were corrected for natural isotopic abundances using IsoCor software (Millard et al. Bioinformatics 28:1294-1296 (2012)). Data from parallel labeling experiments were fit to a single metabolic model as described in Schwender et al. (J. Biol. Chem. 281:34040-34047 (2006)).

Figures 4A, 4B:
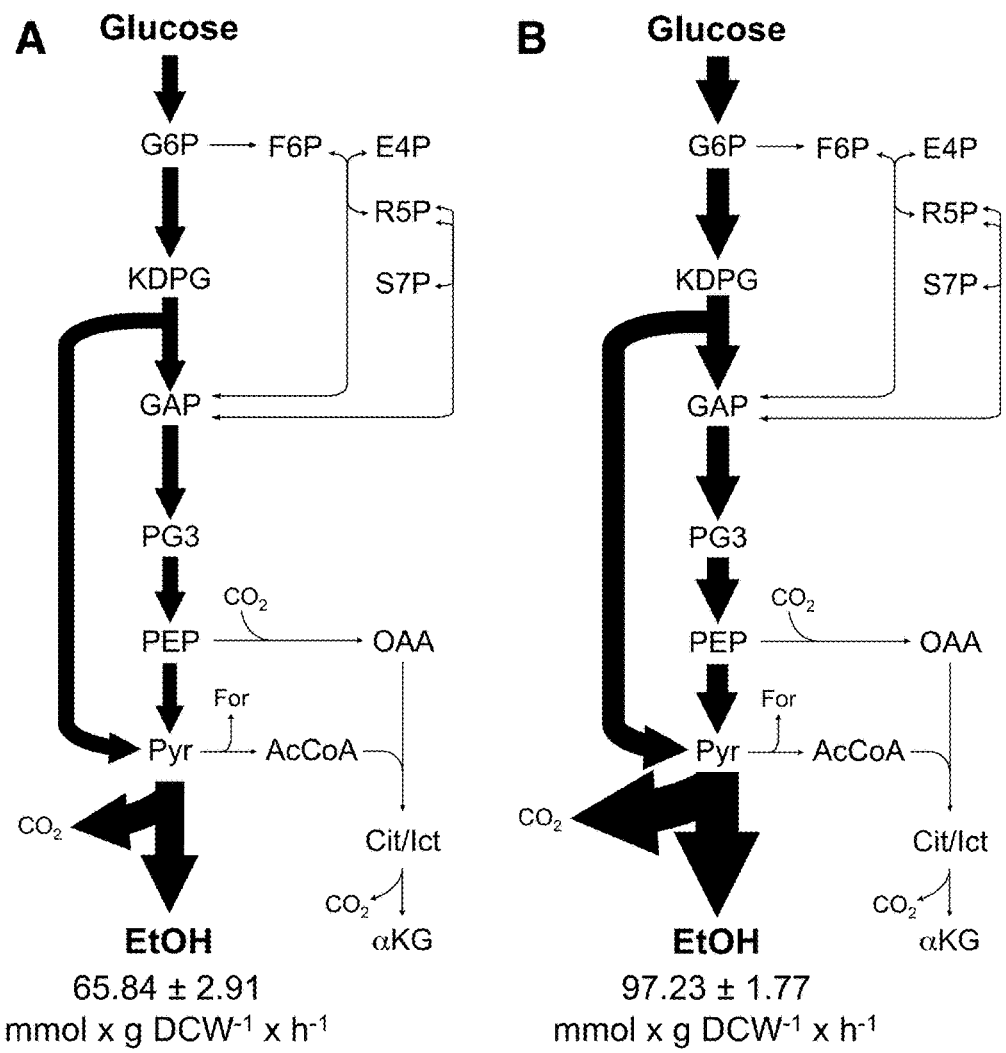
FIGS. 4A & 4B depict absolute net metabolic fluxes during growth in a chemically defined medium with $^{13}C$-labeled glucose and either $NH_4^+$ (FIG. 4A) or $N_2$ (FIG. 4B) determined using $^{13}C$-labeling patterns from proteinaceous amino acids, measured extracellular fluxes, and biomass composition. The thickness of the arrow is proportional to the flux carried by a pathway or reaction. The thinnest arrows represent reactions with a rate of 0.83 mmol×g $DCW^{-1}×h^{-1}$. Values with standard deviations are in Table 3.

The resulting fluxes (normalized to glucose uptake rates) were similar regardless of whether $N_2$ or $NH_4^+$ was provided (Table 3). The absolute central metabolic rates were higher during growth with $N_2$ compared to growth with $NH_4^+$, whereas biosynthetic rates were lower (see FIGS. 4A and 4B, see also Table 3). The data describe a metabolic network that rigidly dedicates flux to ethanol, but is flexible in its overall metabolic rate (FIGS. 4A and 4B, see also Table 3).

TABLE 3

Net metabolic flux distributions and standard deviations determined using $^{13}$C-labeling patterns.

| | Normalized Flux (mole % of glucose uptake rate) | | Absolute flux (mmol × g DCW$^{-1}$ × h$^{-1}$) | |
|---|---|---|---|---|
| Reaction | $NH_4^+$ | $N_2$ | $NH_4^+$ | $N_2$ |
| Glucose → G6P | 100 ± 0.38 | 100 ± 0.21 | 36.43 ± 0.14 | 50.99 ± 0.11 |
| Central metabolism | | | | |
| G6P → Pyr + GAP | 99.69 ± 0.38 | 99.85 ± 0.21 | 36.32 ± 0.14 | 50.91 ± 0.11 |
| G6P → F6P | 0.19 ± 0.01 | 0.09 ± 0.01 | 0.07 ± 0.00 | 0.05 ± 0.01 |
| GAP → 3PG | 99.41 ± 0.38 | 99.73 ± 0.21 | 36.22 ± 0.14 | 50.85 ± 0.11 |
| 3PG → PEP | 97.85 ± 0.42 | 99.00 ± 0.23 | 35.65 ± 0.15 | 50.48 ± 0.12 |
| PEP → Pyr | 89.00 ± 0.24 | 94.54 ± 0.14 | 32.42 ± 0.09 | 48.21 ± 0.07 |
| F6P + GAP → E4P + R5P | 0.14 ± 0.01 | 0.07 ± 0.01 | 0.05 ± 0.00 | 0.04 ± 0.01 |
| R5P + R5P → GAP + S7P | 0.00 ± 0.04 | 0.07 ± 0.01 | 0.00 ± 0.01 | 0.04 ± 0.01 |
| Pyr → EtOH | 180.74 ± 7.98 | 190.69 ± 3.48 | 65.84 ± 2.91 | 97.23 ± 1.77 |

TABLE 3-continued

Net metabolic flux distributions and standard deviations
determined using $^{13}$C-labeling patterns.

| Reaction | Normalized Flux (mole % of glucose uptake rate) | | Absolute flux (mmol × g DCW$^{-1}$ × h$^{-1}$) | |
|---|---|---|---|---|
| | $NH_4^+$ | $N_2$ | $NH_4^+$ | $N_2$ |
| Cit → αKG + CO2 | 5.49 ± 0.35 | 2.81 ± 0.19 | 2.00 ± 0.13 | 1.43 ± 0.10 |
| OAA + AcCoA→ Cit | 5.49 ± 0.35 | 2.81 ± 0.19 | 2.00 ± 0.13 | 1.43 ± 0.10 |
| PEP + CO$_2$ → OAA | 8.63 ± 0.33 | 4.39 ± 0.18 | 3.14 ± 0.12 | 2.24 ± 0.09 |
| Pyr → AcCoA + C1 | 5.83 ± 0.4 | 2.86 ± 0.23 | 2.12 ± 0.15 | 1.46 ± 0.12 |
| Biosynthetic reactions | | | | |
| AcCoA→ | 1.84 ± 0.19 | 0.85 ± 0.09 | 0.67 ± 0.07 | 0.43 ± 0.05 |
| E4P → | 0.14 ± 0.01 | 0.07 ± 0.01 | 0.05 ± 0.00 | 0.04 ± 0.01 |
| F6P → | 0.05 ± 0.00 | 0.02 ± 0.00 | 0.02 ± 0.00 | 0.01 ± 0.00 |
| GAP → | 0.13 ± 0.01 | 0.06 ± 0.01 | 0.05 ± 0.00 | 0.03 ± 0.01 |
| G6P → | 0.12 ± 0.01 | 0.06 ± 0.01 | 0.04 ± 0.00 | 0.03 ± 0.01 |
| OAA → | 1.65 ± 0.16 | 0.77 ± 0.08 | 0.60 ± 0.06 | 0.39 ± 0.04 |
| PEP → | 0.22 ± 0.02 | 0.07 ± 0.01 | 0.08 ± 0.01 | 0.04 ± 0.01 |
| 3PG→ | 1.56 ± 0.15 | 0.72 ± 0.07 | 0.57 ± 0.05 | 0.37 ± 0.04 |
| R5P → | 0.14 ± 0.07 | 0.07 ± 0.03 | 0.05 ± 0.03 | 0.04 ± 0.02 |
| αKG → | 5.49 ± 0.35 | 2.81 ± 0.19 | 2.00 ± 0.13 | 1.43 ± 0.10 |

Example 3

In this Example, it was determined whether $N_2$ fixation would occur during growth on a cellulosic feedstock.

Z. mobilis (ZM4) was cultured in a dilute acid hydrolysate of Miscanthus x giganteus grass that had been grown without fertilizer. Cultures were grown in 10-ml volumes in 27-ml anaerobic test tubes. Test tubes were laid flat and shaken at 225 rpm. The hydrolysate simulated the amount of nitrogen expected to be available in an industrial medium, but not necessarily other industrial parameters.

Miscanthus hydrolysate medium was prepared as described in Sedlak & Ho (Appl. Biochem. Biotechnol. 113-116:403-16 (2004)) with some modifications. Miscanthus x giganteus was grown without fertilizer at the Energy Biosciences Institute, Urbana, Ill. It was harvested, dried, and chopped. Briefly, 100 grams was hydrolyzed in 1% $H_2SO_4$ for 1 hour at 121° C. The hydrolysate was filtered and the pH adjusted to 10 with CaOH$_2$ and heated to 50° C. for 30 minutes. The hydrolysate was then cooled to room temperature and the pH was adjusted to 6 using $H_3PO_4$. Precipitate was removed by filtration with Whatman filter paper and the liquid was then filter sterilized using a 0.2 micron filter followed by 1:1 dilution with water. Various supplements were added as indicated at the following concentrations: trace elements (0.1% v/v), $(NH_4)_6Mo_7O_{24}\cdot 4H_2O$ (0.026 mg/L), $FeSO_4\cdot 7H_2O$ (0.71 mg/L), clarified corn steep liquor (Sigma), and calcium pantothenate (105 nM). Corn steep liquor (CSL) was clarified by centrifugation at 16,000 xg for 5 minutes. The diluted hydrolysate contained 25 mM of glucose and 56 mM of xylose. Additional glucose was added to raise the concentration to 71 mM. Two additional glucose supplements of 500 μmoles each were added during the fermentation to simulate the total amount of sugar expected if cellulases were used to liberate additional glucose, and if a strain capable of xylose utilization, such as is disclosed in WO 1998050524A1, which is incorporated by reference to the extent it is consistent herewith, was used. Excess gas was expelled between each addition of glucose to lower the pressure in the tubes as a safety precaution. Tubes were flushed with either $N_2$ or Ar as appropriate after each addition of glucose. Another set of tubes did not receive additional $N_2$ supplements to test whether $N_2$ was limiting.

Cell density was assayed by optical density at 660 nm using a Genesys 20 visible spectrophotometer (Thermo-Fisher). Substrate and products were quantified using a Shimadzu high performance liquid chromatograph as described in McKinlay et al. (Appl. Environ. Microbiol. 71:6651-6656 (2005)).

The lowest level of growth was observed when no nitrogen supplements were provided (FIG. 1; Ar+Te). The addition of $N_2$ gas resulted in a 1.4-fold higher cell density when trace elements were omitted ($N_2$), and a 2-fold higher cell density when trace elements were provided ($N_2$+Te). The Fe and Mo concentrations that limit growth of $N_2$-fixing Z. mobilis (ZM4) in miscanthus hydrolysate medium were identified (see FIG. 2). Particularly, miscanthus hydrolysate was prepared with $N_2$ as the major nitrogen source and with three separate glucose supplements to simulate sugar that would be released by cellulases. For iron-limitation experiments (FIG. 2A) the $(NH_4)_6Mo_7O_2\cdot 4\cdot 4H_2O$ concentration was constant at 0.026 mg/L. For molybdenum-limitation experiments (FIG. 2B) the $FeSO_4\cdot 7H_2O$ concentration was constant at 0.71 mg/L. Mo and Fe, the two nitrogenase metal cofactors, were the only trace elements required to achieve this 2-fold higher cell level ($N_2$+Fe+Mo), and trace elements were not limiting, since doubling their concentration did not affect the final cell density ($N_2$+2×Te) (FIG. 1). Separately, $N_2$ was not limiting, as final cell densities were the same with and without additional $N_2$ supplements during culturing (data not shown). Likewise, the hydrolysate contained sufficient essential pantothenate vitamin, since the addition of pantothenate did not affect the final growth level (FIG. 1). The highest level of growth with $N_2$ was comparable to that seen when 1% CSL was provided. The ethanol yield from the '$N_2$+Fe+Mo' condition was 97±2% of the theoretical maximum, which was slightly higher than the 94±1% observed with 1% CSL (t-test, P<0.05). The minimum concentration of $(NH_4)_6Mo_7O_{24}\cdot 4H_2O$ and $FeSO_4\cdot 7H_2O$ to support full growth of Z. mobilis in miscanthus hydrolysate were identified as 0.026 mg/L and 0.355 mg/L, respectively (see FIG. 2). Thus, when provided with the necessary cofactors for nitrogenase activity, $N_2$ can substitute for CSL as a nitrogen supplement under these simulated industrial conditions.

Example 4

In this Example, the ability of *Zymomonas mobilis* (*Z. mobilis*) to grow and produce ethanol with different volumes of $N_2$ gas was determined.

10 mL batch cultures were grown in an anaerobic chemically defined medium with 17 mL of headspace. All cultures were laid horizontally and shaken at 225 rpm. Cultures were incubated at 30° C.

Figures 5A, 5B:
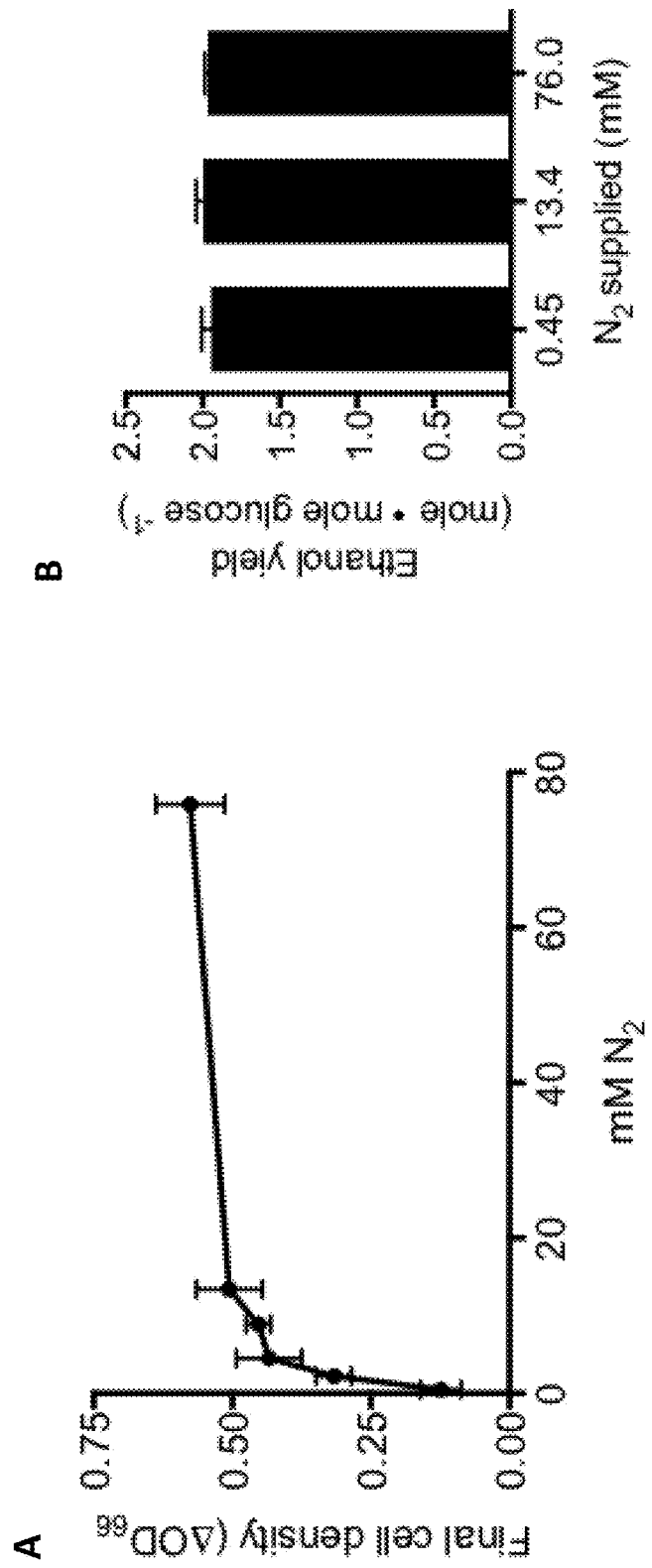
FIGS. 5A & 5B depict the effect of the amount of supplied $N_2$ on *Z. mobilis* (ZM4) growth (A) and ethanol yield (B) in 10 mL batch cultures grown in an anaerobic chemically defined medium with 17 mL of headspace. All cultures were laid horizontally and shaken at 225 rpm. Cultures were incubated at 30° C. Error bars are s.d. (n=3-9). The volumes of $N_2$ gas added were as follows: 0.1 mL=0.45 mM; 0.5 ml=2.2 mM; 1 ml=4.5 mM; 2 ml=8.9 mM; 3 ml=13.4 mM; 17 ml=76.0 mM. The rest of the headspace gas was argon.

As shown in FIG. 5A, the amount of $N_2$ provided limited the amount of *Z. mobilis* growth when supplied at an amount below 13.4 mM (mM of $N_2$ in the vessel per liter of culture liquid). The ethanol yield generated by *Z. mobilis* was not affected by the amount of $N_2$ supplied, as ethanol yields near the theoretical maximum of 2 moles of ethanol per mole of glucose consumed were observed even when only 0.45 mM $N_2$ was supplied (FIG. 5B).

Example 5

In this Example, the effect of temperature on the ability of *Zymomonas mobilis* (*Z. mobilis*) to grow and produce ethanol was determined.

10 mL batch cultures were grown in an anaerobic chemically defined medium with a full $N_2$ headspace at 22° C., 30° C., 37° C., 40° C. and 42° C. All cultures were laid horizontally and shaken at 225 rpm. Only 12% of the glucose was consumed in the samples at 40° C. at the time of sampling (98 h) due to the low amount of growth.

Figure 6A:
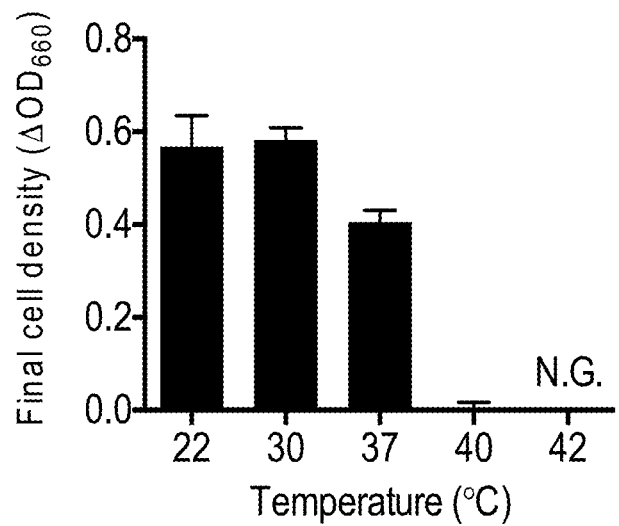
FIGS. 6A & 6B depict the effect of temperature on *Z. mobilis* (ZM4) growth (A) and ethanol yield (B) in 10 mL batch cultures grown in an anaerobic chemically defined medium with a full $N_2$ headspace. All cultures were laid horizontally and shaken at 225 rpm. Cultures were incubated at 30° C. Error bars are s.d. (n=3). Only 12% of the glucose was consumed in the samples at 40° C. at the time of sampling (98 h) due to the low amount of growth. N.G., no growth; N.D., not determined.
Figure 6B:
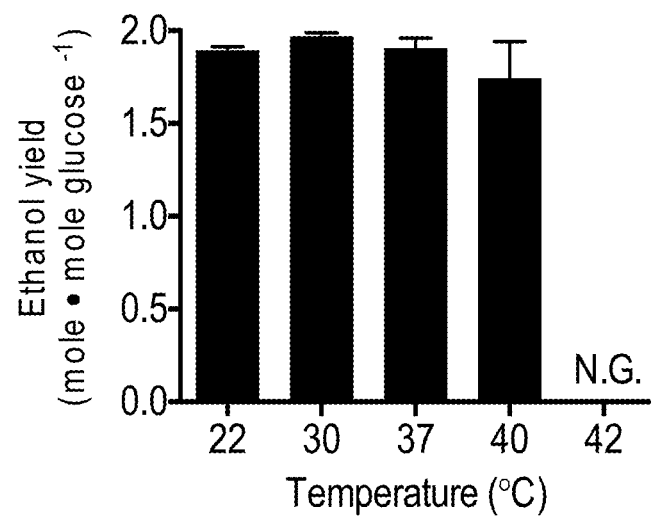

As shown in FIG. 6A, *Z. mobilis* could grow with $N_2$ gas as the sole nitrogen source up to a temperature of 40° C. At 37° C., the amount of growth was about two-thirds that observed at 22° C. and 30° C. At 40° C., growth was severely limited, as was glucose consumption, within the 98 h observation period (FIG. 6A). At all temperatures where growth was observed, *Z. mobilis* generated an ethanol yield near the theoretical maximum of 2 moles of ethanol per mole of glucose consumed (FIG. 6B).

Example 6

In this Example, the effect of pH on *Zymomonas mobilis* (*Z. mobilis*) to grow and produce ethanol was determined.

10 mL batch cultures were grown in an anaerobic chemically defined medium with a full $N_2$ headspace. All cultures were laid horizontally and shaken at 225 rpm. Cultures were incubated at 30° C. pH was adjusted using either 1M NaOH or 1M HCl with 1M NaCl to maintain osmolarity as follows: pH 3.6, 70 μL HCl+100 μL NaCl; pH 4.5, 65 μL HCl +100 μL NaCl; pH 6.1, 50 μL HCl+100 μL NaCl; pH 7, 100 μL NaCl; pH 8.2, 70 μL NaOH+30 μL NaCl; pH 9.2, 80 μL NaOH+10 NaCl; and pH 11.1, 100 μL NaOH. Ethanol yield was not determined at pH 3.6 and 11.1 due to a lack of growth and/or glucose consumption.

Figure 7A:
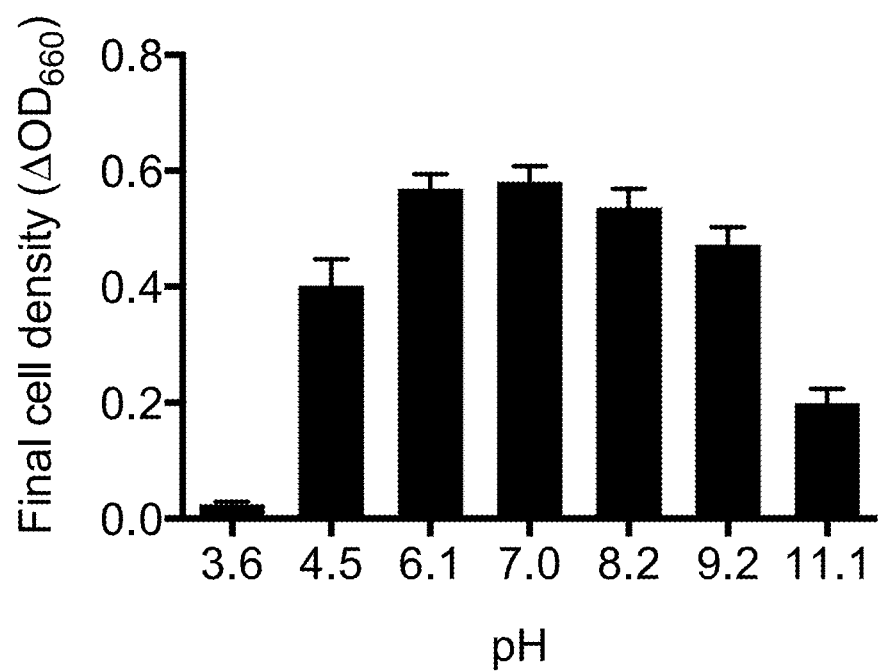
FIGS. 7A & 7B depict the effect of initial pH on *Z. mobilis* (ZM4) growth (A) and ethanol yield (B) in 10 mL batch cultures grown in an anaerobic chemically defined medium with a full $N_2$ headspace. All cultures were laid horizontally and shaken at 225 rpm. Cultures were incubated at 30° C. Error bars are s.d. (n=3). pH was adjusted using either 1M NaOH or 1M HCl with 1M NaCl to maintain osmolarity as follows: pH 3.6, 70 μL HCl+100 μL NaCl; pH 4.5, 65 μL HCl+100 μL NaCl; pH 6.1, 50 μL HCl+100 μL NaCl; pH 7, 100 μL NaCl; pH 8.2, 70 μL NaOH+30 μL NaCl; pH 9.2, 80 μL NaOH+10 NaCl; pH 11.1, 100 μL NaOH. Ethanol yield was not determined at pH 3.6 and 11.1 due to a lack of growth and/or glucose consumption.
Figure 7B:
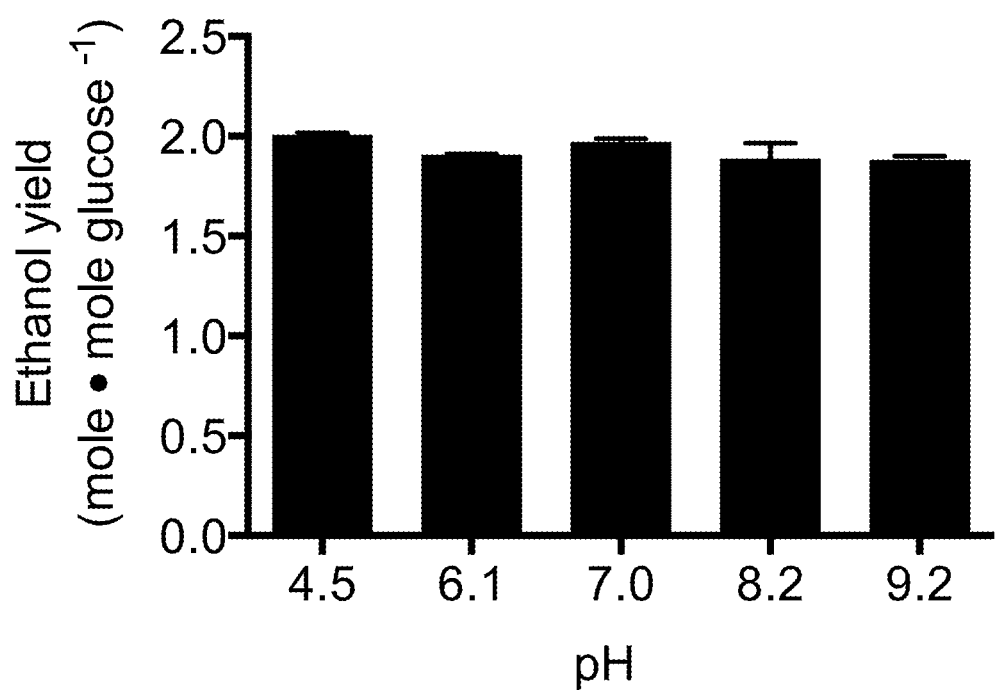

As shown in FIG. 7A, *Z. mobilis* grew with $N_2$ gas as the sole nitrogen source when the initial pH was between 4.5 and 9.2. The increase in optical density observed at pH 11.1 was unlikely due to growth, since negligible glucose consumption and ethanol production were observed, suggesting that the increase in optical density was due to a factor other than growth, such as the precipitation of minerals. Final cell densities were notably lower outside of an initial pH range of 6.1 to 8.2 (FIG. 7A). At all initial pH conditions where growth was observed, *Z. mobilis* generated an ethanol yield near the theoretical maximum of 2 moles of ethanol per mole of glucose consumed (FIG. 7B).

The above results demonstrate the use of $N_2$ as an alternative nitrogen source for cellulosic ethanol production by *Z. mobilis*.

This written description uses examples to disclose the invention and also to enable any person skilled in the art to practice the present disclosure, including making and using any mediums or systems and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A composition for producing a cellulosic bioalcohol, the composition comprising:
   a bioalcohol producing, $N_2$ gas-fixing bacteria in genus *Zymomonas* that assimilates $N_2$ gas as its sole nitrogen source during bioalcohol production after nitrogen in a cellulosic feedstock is depleted;
   an anaerobic culture medium that lacks a soluble nitrogen compound supplement, the medium comprising a hydrolysate of the cellulosic feedstock, iron, and molybdenum; and,
   a $N_2$ gas in fluid communication with the anaerobic culture medium, where the sole nitrogen source for the bioalcohol producing, $N_2$ gas-fixing bacteria in the genus *Zymomonas* during cellulosic bioalcohol production after the nitrogen in the cellulosic feedstock is depleted is the $N_2$ gas.

2. The composition for producing a cellulosic bioalcohol of claim 1, where the anaerobic culture medium comprises: $Na_2HPO_4$, $KH_2PO_4$, and NaCl in a molar ratio of 1:1.2:1.5.

3. The composition for producing a cellulosic bioalcohol of claim 1, where the anaerobic culture medium comprises: $Na_2HPO_4$, $KH_2PO_4$, NaCl, and trace elements, where the trace elements comprise: nitrilotriacetic acid, $MgSO_4$, $CaCl_2 \cdot 2H_2O$, $(NH_4)_6Mo_7O_{24} \cdot 4H_2O$, $FeSO_4 \cdot 7H_2O$, ethylenediaminetetraacetic acid, $ZnSO_4 \cdot 7H_2O$, $MnSO_4 \cdot H_2O$, $CuSO_4 \cdot 5H_2O$, $Co(NO_3)_2 \cdot 6H_2O$, and $Na_2B_4O_7 \cdot 10H_2O$.

4. The composition for producing a cellulosic bioalcohol of claim 1, where the bioalcohol production is production of a bioalcohol selected from the group consisting of bioethanol, biopropanol, and biobutanol.

5. The composition for producing a cellulosic bioalcohol of claim 1, where the bioalcohol producing, $N_2$ gas-fixing bacteria in the genus *Zymomonas* that assimilates $N_2$ gas as its sole nitrogen source during bioalcohol production is *Zymomonas mobilis*.

6. The composition for producing a cellulosic bioalcohol of claim 1, where the bioalcohol producing, $N_2$ gas-fixing bacteria in the genus *Zymomonas* that assimilates $N_2$ gas as its sole nitrogen source during bioalcohol production is *Zymomonas mobilis* ZM4.

7. The composition for producing a cellulosic bioalcohol of claim 1, where the anaerobic culture medium that lacks a soluble nitrogen compound supplement further comprises a phosphate source.

8. The composition for producing a cellulosic bioalcohol of claim 1, where the anaerobic culture medium that lacks a soluble nitrogen compound supplement further comprises NaCl.

9. The composition for producing a cellulosic bioalcohol of claim 1, where the anaerobic culture medium that lacks a soluble nitrogen compound supplement lacks a soluble nitrogen compound selected from the group consisting of ammonium, corn steep liquor (CSL) diammonium phosphate (DAP), ammonium hydroxide and other ammonium salts.

10. The composition for producing a cellulosic bioalcohol of claim 1, where the composition has a temperature from 20° C. to 40° C.

11. The composition for producing a cellulosic bioalcohol of claim 1, where the composition has a pH ranging from 4 to 9.2.

12. The composition for producing a cellulosic bioalcohol of claim 1, where a concentration of the $N_2$ gas is from 0.45 mM to 76 mM per liter of the composition.

13. The composition for producing a cellulosic bioalcohol of claim 1, where the anaerobic culture medium comprises: $Na_2HPO_4$, $KH_2PO_4$, NaCl, and trace elements, wherein the trace elements comprise: nitrilotriacetic acid, $MgSO_4$, $CaCl_2 \cdot 2H_2O$, $(NH_4)_6Mo_7O_{24} \cdot 4H_2O$, $FeSO_4 \cdot 7H_2O$, ethylenediaminetetraacetic acid, $ZnSO_4 \cdot 7H_2O$, $MnSO_4 \cdot H_2O$, $CuSO_4 \cdot 5H_2O$, $Co(NO_3)_2 \cdot 6H_2O$, and $Na_2B_4O_7 \cdot 10H_2O$.

14. The composition for producing a cellulosic bioalcohol of claim 1, where the $N_2$ gas is present at a concentration of 0.45 mM to 76 mM per liter of the anaerobic culture medium.

15. The composition for producing a cellulosic bioalcohol of claim 1, where the $Na_2HPO_4$ and said $KH_2PO_4$ are present in a molar ratio of 1:1.2.

16. The composition for producing a cellulosic bioalcohol of claim 1, where the bioalcohol production is bioethanol production.

17. The composition for producing a cellulosic bioalcohol of claim 1, where the $N_2$ gas-fixing bacteria comprises a nitrogenase enzyme.

18. A composition for producing a cellulosic bioethanol, the composition consisting essentially of:
a bioalcohol producing, $N_2$ gas-fixing bacteria in genus *Zymomonas* that assimilates $N_2$ gas as its sole nitrogen source during bioalcohol production after nitrogen in a cellulosic feedstock is depleted;
an anaerobic culture medium that lacks a soluble nitrogen compound supplement, the medium consisting essentially of a hydrolysate of the cellulosic feedstock, iron, and molybdenum; and,
a $N_2$ gas in fluid communication with the anaerobic culture medium, where the sole nitrogen source for the bioalcohol producing, $N_2$ gas-fixing bacteria in the genus *Zymomonas* during cellulosic bioalcohol production is the $N_2$ gas after the nitrogen in the cellulosic feedstock is depleted.

19. A composition for producing a cellulosic ethanol, the composition consisting of:
a bioalcohol producing, $N_2$ gas-fixing bacteria in genus *Zymomonas* that assimilates $N_2$ gas as its sole nitrogen source during bioalcohol production after nitrogen in a cellulosic feedstock is depleted;
an anaerobic culture medium that lacks a soluble nitrogen compound supplement, the medium consisting of a hydrolysate of the cellulosic feedstock, iron, and molybdenum; and,
a $N_2$ gas in fluid communication with the anaerobic culture medium, where the sole nitrogen source for the bioalcohol producing, $N_2$ gas-fixing bacteria in the genus *Zymomonas* during cellulosic bioalcohol production is the $N_2$ gas after the nitrogen in the cellulosic feedstock is depleted.

\* \* \* \* \*